United States Patent [19]

Maeda et al.

[11] 4,446,136

[45] May 1, 1984

[54] AGENTS FOR IMPROVEMENT OF PERIPHERAL BLOOD FLOW

[75] Inventors: Hiroshi Maeda; Katsuhide Nishi, both of Kumamoto, Japan

[73] Assignee: Yamanouchi Pharmaceutical Co., Ltd., Tokyo, Japan

[21] Appl. No.: 304,943

[22] Filed: Sep. 23, 1981

[30] Foreign Application Priority Data

Sep. 25, 1980 [JP] Japan .................................. 55-132336

[51] Int. Cl.³ ............................................... A61K 37/12
[52] U.S. Cl. ..................................... 424/177; 260/117
[58] Field of Search ......................... 424/177; 260/117

[56] References Cited

U.S. PATENT DOCUMENTS

| | | | |
|---|---|---|---|
| 2,591,133 | 5/1950 | Campbell et al. | 424/177 |
| 3,035,982 | 5/1962 | Hanus | 424/177 |
| 3,057,782 | 10/1962 | Lindner et al. | 424/177 |
| 3,163,543 | 12/1964 | Gorfinkle | 424/177 |
| 3,794,729 | 2/1974 | Wohl et al. | 424/337 |
| 4,061,731 | 12/1977 | Gottlieb | 424/101 |
| 4,164,559 | 8/1979 | Miyata et al. | 424/19 |
| 4,178,361 | 12/1979 | Cohen et al. | 424/81 |
| 4,191,747 | 3/1980 | Scheicher | 424/180 |
| 4,224,328 | 9/1980 | Takesue | 424/251 |
| 4,362,718 | 12/1982 | Maeda et al. | 424/177 |

*Primary Examiner*—Jane T. Fan
*Attorney, Agent, or Firm*—Burgess, Ryan & Wayne

[57] ABSTRACT

Agents for improving blood circulation containing gelatin or solubilized collagen as the effective component. The agents facilitate and restore impaired peripheral blood flow, prevent the occurence of circulatory insufficiency, stabilize plasma cells, prevent coagulation of blood, and improve maintenance of various devices for assisting extracorporeal circulation.

17 Claims, 7 Drawing Figures

AGENTS FOR IMPROVEMENT OF PERIPHERAL BLOOD FLOW

FIELD OF THE INVENTION

The invention described here includes medicaments which facilitate and restore impaired peripheral blood flow, prevent the occurence of circulatory insufficiency, stabilize plasma cells, prevent coagulation of blood, and improve maintenance of various devices for assisting extracorporeal circulation.

BACKGROUND OF THE INVENTION

The blood of the physiologically healthy man and animal, contains more than 50% insoluble components, mainly in the form of plasma cells. These components of blood flow at high speed through capillaries having a diameter less than $5\mu$, in spite of the fact the diameter of plasma cells such as erythrocytes or leucocytes is $5-10\mu$ and sometimes larger than the capillaries. Consequently, to attain smooth passage of blood through the small capillary, distension of the capillary wall as well as deformation of the plasma cells is substantially required. The present inventors have indicated that friction between plasma cells and the vessel wall is an important factor in maintaining blood flow in microcirculation. Various pathological conditions or diseases may result from or be aggravated by lack of lubrication of the cells, namely peripheral thrombosis, phlebo-thrombosis, cerebral thrombosis, ischemic heart disease, plasma cell sludging, disseminated intravascular coagulation, other microcirculatory failures, platelets agglutination or bleeding caused by excessive hemolysis in cancer patients under treatment with antitumore agents. Furthermore, in devices for assisting extracorporeal circulation fine tubings with poor lubrication and distensibility result in frequent troubles due to accompanying hemolysis even after their use for a short period of time.

The inventors have been engaged for a long period of time in investigating methods or treatments of preventing damage to blood cells during the passage of the cells through the capillary which may lead to the alleviation of the pathological conditions associated with the previously mentioned diseases. The inventors have already filed patent applications on a process of producing stable protein solutions (Japanese Pat. Appln. Laid-open No. 37,187/'78) and substances for improvement of peripheral circulation using a glycoprotein (Japanese Pat. Appln. Laid-open No. 15,213/'81).

SUMMARY OF THE INVENTION

The inventors have found that gelatin or solubilized collagen affects on the occurrence of coagulation, agglutination and hemolysis of solid components of blood, such as erythrocytes, leucocytes, thereby facilitating the filtration and passage of blood in capillaries, artificial membranes (e.g., nitrocellulose membranes, cellulose acetate membranes, Teflon membranes, etc.,), artificial fine tubes for extracorporeal circulation, and devices which assist extracorporeal circulation, at the same time preventing or reducing stagnation of blood in micropores, as well as stabilizing the plasma cell membrane, and facilitating microcirculation of the blood cell components. Based on findings described above, the inventors have completed the present invention.

The invention covers substances for improvement of peripheral blood flow comprising gelatin or solubilized collagen as the effective component.

DETAILED DESCRIPTION OF THE INVENTION

Figure 1A:
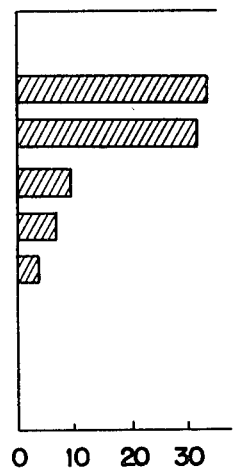
FIG. 1A shows the effect of gelatin on the ratio of filtration of erythrocytes through micropores and FIG. 1B shows the ratio of hemolysis which occured during filtration. The effects were compared with those of other substances.

Gelatin and collagen which are the active components in this invention are known substances as described in, for example, Haurowits, "The Chemistry and Function of Proteins"; 212–217 (1963, Academic Press, N.Y.). The substances can be easily obtained from cutaneous tissues, bones, hide etc., of animals after solubilization. Furthermore, commercially available gelatin or collagen having adequate purity can be used for this invention. In the case of insoluble collagen, the solubility thereof can be increased by subjecting the collagen to chemical modifications such as maleylation, succinylation, citraconylation, formylation, etc., or a partial hydrolysis such as by autoclaving, a hydrochloric acid treatment, a liquid ammonia treatment, cyanogen bromide treatment, collagenase treatment, elastase treatment, etc. Thus, insoluble collagen can be prepared as solubilized collagen.

These substances are effective for facilitating blood circulation can be generally used as an injection ingredient, and the injection ingredient of this invention may be used as a combination with various injection ingredients such as physiological saline solution, nutrientia, drip-infusion pharmacon, blood-transfusion materials, etc. In this invention, gelatin, solubilized collagen, or a mixture of gelatin and solubilized collagen can be added to other various solutions for intravenous or intraarterial injection, and the desired effect can be usually obtained at concentrations of 0.01–1.0% by volume.

Furthermore, according to another embodiment of the invention, these substances may be added to blood or a blood cell suspension, serum, blood plasma, artificial nutrient solutions, plasma-expander, cell suspension, and concentrated erythrocyte transfusion, etc., at concentrations of 1 $\mu$g/ml to 200 mg/ml. Furthermore, the substances of this invention can be used as a solution for various devices for assisting extracorporeal circulation.

The substances can be administered to the circulatory system as a pretreatment for preventing damage to erythrocytes and for coagulation during extracorporeal circulation. The substances of this invention may be administered in doses of 0.1–10 g dose 1 to 3 times per day for patients with a body weight of 60 kg but a larger amount thereof may be administered. When the substances of this invention are administered in a local cerebral microartery, it is preferred to administer the substances of this invention in single doses of 0.01–1.0 g, 1–10 times per day depending on the patients.

The invention will be further detailed as follows.

EXPERIMENT 1

Preparation of solubilized collagen

Method I (Succinylation of collagen):

10 ml of water or aqueous 7% sodium bicarbonate solution was added to 1 g of insoluble collagen, and the mixture was autoclaved at 120° C. for 30–120 min. Then, after cooling the reaction mixture to room temperature, the pH was adjusted to 8.0 and 1 g of powdered succinic anhydride was added to the reaction mixture very slowly to allow a sufficient period of time for reaction. The reaction was carried out for 2–3 hours under a proper pH-control with a pH-stat. However, the reaction may be conducted at a pH ranging from 7.5 to 9.5. After the reaction, the product was separated by centrifugation (at 2,000 r.p.m.) and the supernatant was dialyzed against distilled water. The product was lyophilized to yield about 500 mg of sample (1) of succinylated collagen. (yield: about 50% (w/w)).

Method II (Partial hydrolysis and succinylation of collagen):

To 2 g of insoluble collagen were added 20 ml of 6 M hydrochloric acid and the mixture was treated for 2–3 hours at room temperature. Then, the mixture was chilled and neutralized by the addition of aqueous 50% NaOH solution. The product was separated by centrifugation (at 2,000 r.p.m.) and the supernatant was dialyzed against distilled water. During dialysis, precipitates were formed but only the supernatant was lyophilized, which yielded about 330 mg of sample (2). The precipitates formed during the dialysis were treated according to Method I and succinylated. About 440 mg of sample (3) was obtained.

When concentrated hydrochloric acid or sulfuric acid was used in place of 6 M hydrochloric acid in the foregoing methods, similar results were obtained in a shorter period of time than in the above-mentioned.

EXPERIMENT 2

Facilitation of passage of erythrocites through membrane filters (i) Effects of gelatin:

A mixture of 1 part of human blood and 1 part (v/v) of preservative solution (sodium citrate buffer containing glucose) was washed 4 to 5 times with physiological saline solution and then 2% (by volume) erythrocyte solution was prepared in physiological saline. In the next step, physiological saline solutions containing 0.05% gelatin, 0.1% $\alpha_1$-acid glycoprotein, 0.1% polyethylene glycol, 0.1% $\gamma$-globulin, 0.1% ovomucoid, 0.1% dextran, 0.1% dextran sulfate, 0.1% chondroitin sulfate, or physiological saline alone were mixed with an equal volume of the erythrocyte suspension, and then each mixture was shaken mildly for 30 min at 37° C. Thereafter 1 ml of each mixture was subjected to filtration through a nitrocellulose membrane filter (13 mm in diameter and 5 $\mu$m in average size of micropores, made by Sartorius Co.) at 37° C. under a pressure of 80 mmHg/cm$^2$. The filtrate was immediately subjected to centrifugation for 2 min at 1,500 r.p.m. and from the supernatant, the ratio of hemolysis during filtration was calculated based on absorbance at 420 nm. As to the erythrocytes remaining on the filter, 5 ml of deionized water was added to the erythrocytes on the membrane filter by placing into a test tube, and the resulting hemolysis due to hypotonicis permitted a measurement of absorbance at 420 nm to calculate the ratio of filtered erythrocytes through the membrane.

Figure 1B:
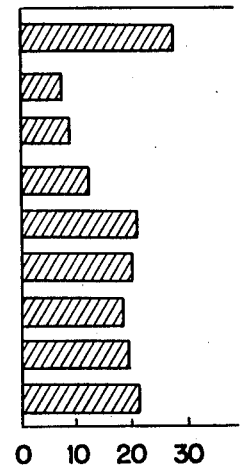

The results are shown in FIG. 1 wherein the control (physiological saline solution alone), showed no erythrocytes passed through the filter. On the other hand, in the saline solution containing 0.05% gelatin, the ratio of passage of erythrocyte increased remarkably and the ratio of hemolysis was reduced. In experiments with other substances blood cells hardly passed through the membrane. Only $\alpha_1$-acid glycoprotein which was already reported by the inventors showed a similar activity of accelerating the passage of erythrocytes through micropores (see, Maeda, Nishi and Mori; "Life Sciences", Vol. 27, No. 2, pages 157–161, 1980).

Experiments on hemolysis by the foregoing filtering method showed that about 25–30% of the erythrocytes were hemolysed in the case of physiological saline solution alone. In the case of human-$\gamma$-globulin and dextran sulfate it was 25–30%. When gelatin and $\alpha_1$-acid glycoprotein were tested only 5 to 7% of the erythrocytes were hemolysed.

Thus, the results show that gelatin facilitates the passage of erythrocytes through micropores and prevents the occurence of hemolysis.

Figure 2A:
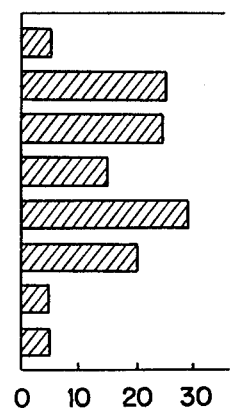
FIG. 2A shows the effect of solubilized collagen on the ratio of filtration of erythrocytes and FIG. 2B shows the ratio of hemolysis. The effects were compared with those of other substances.
Figure 2B:
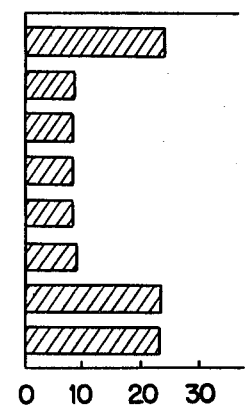

(ii) Effects of solubilized collagen:

Sheep erthrocytes was properly diluted to give 2% (v/v) with physiological saline (pH 7.2) buffered with 0.01 M Na-phosphate. A membrane filter of $3\mu$ in average pore size having a diameter of 13 mm was used. One part of physiological saline containing samples (1), (2), (3), gelatin, dextran $\alpha_1$-acid glycoprotein, serum albumin, at a final concentration of 0.05%, respectively, or saline solution-alone was mixed with 1 part of the above mentioned 2% suspension of sheep erythrocytes. The mixture was shaken for 30 min at 37° C. Thereafter, 1 ml each of the mixture was filtered with the membrane filter under pressure of 80 mmHg/cm$^2$. 0.5 ml of the filtrate was subjected to centrifugation at 1,500 r.p.m. for 2 min and the ratio of hemolysis was determined by measuring absorbance at 420 nm. The remainder of the erythrocytes trapped on the membrane was determined as described above. The results are shown in FIG. 2 and show that the addition of solubilized collagen to 0.05% facilitated the passage of sheep erythrocytes through the micropores, and furthermore reduced the ratio of hemolysis to about 30–40% of the control. This indicates that the medicament of the present invention has lubricant and stabilizing actions on the cell membrane of the erythrocyte, and hence facilitates the passage of erythrocytes through the micropores and prevents hemolysis.

EXPERIMENT 3

Effects of gelatin on microcirculation in vivo

A rabbit was anesthetized with urethane. The abdominal cavity was opened to expose the mesemterium and the blood flow in microvessels was observed under a microscope. Flow and passage of erythrocytes through microvessels was good under normal blood pressure but when the blood pressure was lowered by bleeding or by the administration of pentobarbital, the reduction of the passage of erythrocytes and the stagnation of erytrocytes were observed at an arterial blood pressure of 60–80 mmHg/cm$^2$. When the arterial blood pressure was lowered to 40–60 mmHg/cm$^2$, almost all erythrocytes stagnated in the microcapillaries and also rouleau formation and the separation of plasma from blood cell components were observed.

Continuous intraarterial transfusion or intravenous injection of gelatin in doses of 0.1–1 g/kg prevented the stagnation of erythrocytes, the rouleau formation and the separation of plasma from cell components in fine capillaries, which had been observed at an low arterial blood pressure in the control period. Even at arterial blood pressure of 40–60 mmHg, erythrocytes moved smoothly through the microcapillaries, although at a reduced speed. On the other hand, other substances, such as dextran sulfate immunoglobulin or pure albumin did not exert any actions on microcirculation as observed for gelatin.

From the results described above, it is concluded that gelatin possesses facilitating actions on microcirculation in vivo and might well prevent formation of thrombus in small blood vessels.

EXPERIMENT 4

Dose-response relationships of gelatin on filtration and hemolysis (i) Following procedures similar to the Experiment 2 using a concentration of gelatin between 0–2.0 mg/ml, effects of the substance on the filtration ratios of erythrocytes through the membrane filter and the ratio of hemolysis were examined at various concentrations of gelatin.

Figure 3A:
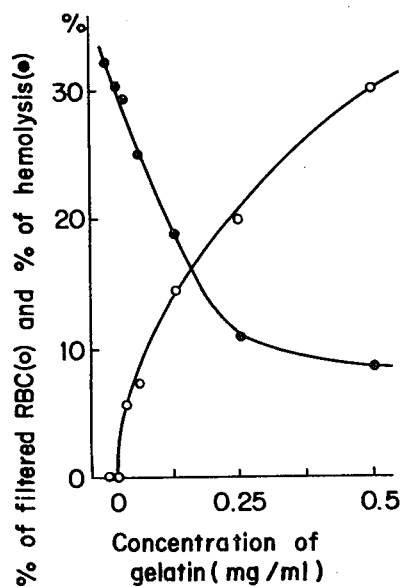
FIGS. 3A and B show dose-response curves of gelatin on the ratio of filtration and hemolysis of erythrocytes.
Figure 3B:
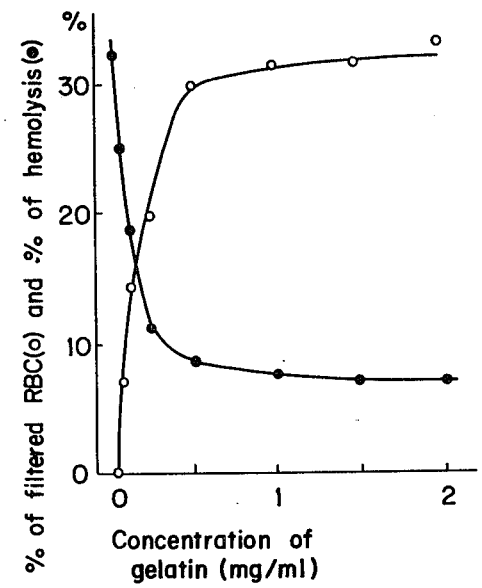

The results are shown in FIG. 3. The filtration ratio reached plateau at concentration of 0.5 mg/ml. A further increase in concentration did not improve the filtration ratio.

Figure 4:
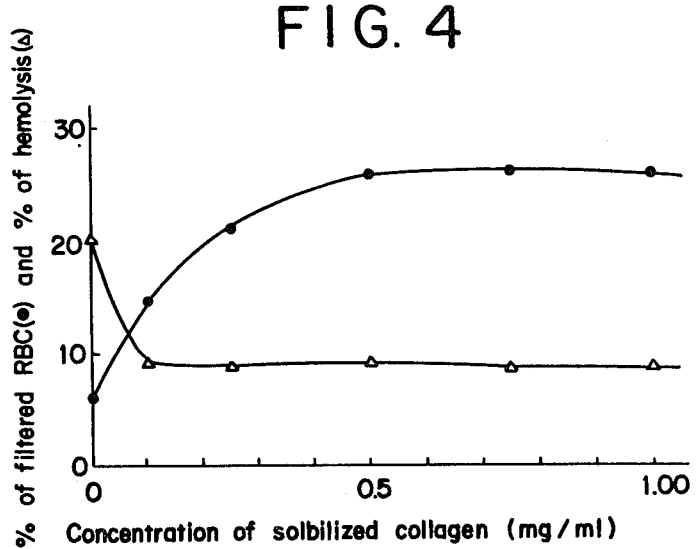
FIG. 4 shows dose-response curves of the solubilized collagen on ratio of filtration and hemolysis of erythrocytes.

(ii) Following the procedures similar to the Experiment 2 using a concentration of 0–1.0 mg/ml of solubilized collagen, the effect of solubilized collagen on the filtration of erythrocytes through the membrane filter at various concentrations of the substance were examined. As shown in FIG. 4, the filtration ratio of erythrocytes reached its peak at a concentration of 0.5 mg/ml of solubilized collagen.

EXPERIMENT 5

Toxicity of gelatin and solubilized collagen

Results of acute toxicity of gelatin and solubilized collagen are summarized in Tables 1, 2 and 3. The results indicate that the acute toxicity of these substances are very mild and hence they appear to be very safe as a medicament for the purposes described above. Gelatin showed no antigenic activity by itself.

TABLE 1

| Animal | ($LD_{50}$ of gelatin) | |
|---|---|---|
| | $LD_{50}$ (mg/ml) | Administration method |
| Rat | >1,000 | intravenous, intraperitoneal, subcutaneous |
| Sheep | >1,000 | intravenous, intraperitoneal, subcutaneous |

TABLE 2

| Animal | ($LD_{50}$ of solubilized collagen) | |
|---|---|---|
| | $LD_{50}$ (mg/ml) | Administration method |
| Mouse | >1,000 | intraperitoneal, subcutaneous |
| Rat | >1,000 | intraperitoneal, subcutaneous |
| Rabbit | >1,000 | intraperitoneal, |

TABLE 2-continued

| Animal | ($LD_{50}$ of solubilized collagen) | |
|---|---|---|
| | $LD_{50}$ (mg/ml) | Administration method |
| | | subcutaneous |

TABLE 3

| Cell | (toxicity of gelatin to cells in culture) |
|---|---|
| | Toxicity (50% growth inhibition) |
| HeLa $S_3$ | >100 μg/ml |
| Lung fibroblasts of human embryo | >100 μg/ml |
| EB virus transformed lymphoblastoid cells P3HR-1 | >100 μg/ml |

The following examples are given to illustrate certain procedures of the present invention, but said invention is not limited thereto.

EXAMPLE 1 (injection)

An intraarterial injection was prepared by dissolving 10 mg of solubilized collagen in 10 ml of physiological solution containing 5% maltose.

EXAMPLE 2 (injection)

An intravenous injection was prepared by dissolving 100 mg of solubilized collagen in 50 ml of an aqueous 0.1% sodium bicarbonate solution containing 5% glucose.

EXAMPLE 3 (injection)

An intravenous injection for drip infusion was prepared by dissolving 1.0 g of solubilized collagen in 500 ml of a 5% maltose-Ringer's solution.

EXAMPLE 4 (solution for infusion)

A solution used for blood transfusion was prepared by dissolving 0.1 g of solubilized collagen in 200 ml of the volume of whole blood transfusion.

EXAMPLE 5 (solution for infusion)

A solution used for blood transfusion was prepared by dissolving 1.0 g of solubilized collagen in 100 ml of a solution for concentrated erythrocyte transfusion.

EXAMPLE 6 (maintenance medium for assisting device)

A Ringer's solution containing 5–20 g/liter of solubilized collagen could be used as a preconditioning solution to be used prior to the start-up of extracorporeal circulation apparatus or assisting device.

EXAMPLE 7 (maintenance medium for assisting device)

A 10% aqueous solution of solubilized collagen could be used as an agent for lubrication and for protecting blood cell membranes. It could be introduced by a three-way cock of the extracorporeal circulation apparatus or assisting device.

EXAMPLE 8–14

Agents were prepared in the same manner as in the above Examples 1–7 using gelatin in place of solubilized collagen.

What is claimed is:

1. A method of improving the peripheral blood flow in a warm blooded animal comprising administering to said warm blooded animal by injection an effective amount of a composition comprising an active agent selected from the group consisting of gelatin and solubilized collagen, and a pharmaceutically acceptable carrier.

2. A method of preventing inadequate peripheral blood flow in a warm blooded animal comprising administering to said warm blooded animal by injection an effective amount of a composition comprising an active agent selected from the group consisting of gelatin and solubilized collagen, and a pharmaceutically acceptable carrier.

3. A method of facilitating the employment of extracorporeal circulation devices in blood containing vessels containing said devices comprising administering to said blood containing vessels an effective amount of a composition comprising an active agent selected from the group consisting of gelatin and solubilized collagen, and a pharmaceutically acceptable carrier.

4. The method of claim 1 wherein said composition is administered to said warm blooded animal by intravenous injection.

5. The method of claim 1 wherein said composition is administered to said warm blooded animal by intra-arterial injection.

6. The method of claim 1, 2 or 3 wherein the effective amount of the active agent is between 1 µg/ml and 200 mg/ml of blood.

7. The method of claim 1, 2 or 3 wherein the active agent is gelatin.

8. The method of claim 1, 2 or 3 wherein the active agent is solubilized collagen.

9. The method of claim 1 wherein said warm blooded animal is a human and the effective amount of the active agent is between 0.01 g and 30 g per day.

10. The method of claim 9 wherein the effective amount of the active agent is between 0.1 g and 10 g, one to three times a day.

11. The method of claim 9 wherein said composition is injected in a local cerebral microartery and the effective amount of the active agent is between 0.01 g and 1.0 g, one to ten times per day.

12. The method of claim 4 or 5 wherein the concentration of said active ingredient is between 0.1 and 1.0 percent by volume.

13. The method of claim 1 further comprising adding said composition to a blood containing transfusion solution and administering said solution to said warm blooded animal.

14. The method of claim 2 wherein said warm blooded animal is a human and the effective amount of the active agent is between 0.01 g and 30 g per day.

15. The method of claim 14 wherein the effective amount of the active agent is between 0.1 g and 10 g, one to three times a day.

16. The method of claim 2 wherein said composition is injected in a local cerebral microartery and the effective amount of the active agent is between 0.01 g and 1.0 g, one to ten times a day.

17. The method of claim 16 wherein the effective amount of the active agent is between 0.01 g and 30 g per day.

* * * * *